United States Patent [19]
Hartman et al.

[11] Patent Number: 5,877,432
[45] Date of Patent: Mar. 2, 1999

[54] MAGNETOSTRICTIVE ACTUATOR

[75] Inventors: George Anthony Hartman, Waynesville; James Raymond Sebastian, Kettering, both of Ohio

[73] Assignee: The University of Dayton, Dayton, Ohio

[21] Appl. No.: 954,132

[22] Filed: Oct. 20, 1997

Related U.S. Application Data

[63] Continuation-in-part of Ser. No. 756,813, Nov. 26, 1996, Pat. No. 5,719,339.

[51] Int. Cl.$^6$ ....................................................... G01L 1/12
[52] U.S. Cl. ........................................ 873/862.69; 73/779
[58] Field of Search ............................. 73/779, 811, 855, 73/862.17, 862.69

[56] References Cited

U.S. PATENT DOCUMENTS

| | | | |
|---|---|---|---|
| 3,639,861 | 2/1972 | Russen | 73/779 |
| 3,994,158 | 11/1976 | Weinhold | 73/798 |
| 4,246,793 | 1/1981 | Fairand et al. | 73/628 |
| 4,308,474 | 12/1981 | Savage et al. | |
| 4,861,149 | 8/1989 | Ealey | 350/611 |
| 5,195,377 | 3/1993 | Garshelis | 73/779 |
| 5,280,725 | 1/1994 | Stengel | 73/779 |
| 5,425,276 | 6/1995 | Gram et al. | 73/816 |
| 5,588,466 | 12/1996 | Benz et al. | 137/831 |
| 5,719,339 | 2/1998 | Hartman et al. | 73/811 |

OTHER PUBLICATIONS

Brochure: *Machine Design*, A Penton Publication, Mar. 21, 1991.
Brochure: *Etrema Terfenol–D*, Etrema Products, Inc.
Brochure: *Profiles in Aerospace*, 1993 Etrema Products, Inc.
Brochure: *Etrema Terfenol—D®Magnetostrictive Actuators*, Etrema Products, Inc.
Brochure: *Now Imaging the Possibilities!*, Etrema Products, Inc.

*Primary Examiner*—Richard Chilcot
*Assistant Examiner*—Max H. Noori
*Attorney, Agent, or Firm*—Killworth, Gottman, Hagan & Schaeff, L.L.P.

[57] ABSTRACT

A magnetostrictive actuator is provided comprising an actuator base, a magnetostrictive assembly, an actuator frame, and a flexible disk. The magnetostrictive assembly includes a magnetostrictive element. A first end of the magnetostrictive element is mechanically coupled to the actuator base. A first portion of the actuator frame is mechanically coupled to the actuator base. The flexible disk includes a perimetrical disk portion and a bearing surface portion. The perimetrical disk portion is mechanically coupled to the second frame portion and the bearing surface portion is mechanically coupled to the second magnetostrictive element end portion. The magnetostrictive actuator comprises a magnetostrictive material portion and a plurality of cooling fluid bores formed within the magnetostrictive material portion. Further, the magnetostrictive actuator may comprise an epoxy matrix, a plurality of cooling fluid bores formed within the epoxy matrix, and a plurality of magnetostrictive rods formed within the epoxy matrix.

9 Claims, 8 Drawing Sheets

MAGNETOSTRICTIVE ACTUATOR

CROSS REFERENCE TO RELATED APPLICATIONS

This application is a Continuation-in-Part of U.S. Pat. application No. 08/756,813, filed Nov. 26, 1996, U.S. Pat. No. to 5,719,339.

STATEMENT REGARDING FEDERALLY SPONSORED RESEARCH

The United States Government has rights in this invention pursuant to U.S. Air Force Contract No. F33615-95-C-5819.

BACKGROUND OF THE INVENTION

The present invention relates to an improved actuator and, more specifically, to a magnetostrictive actuator.

Figure 8:
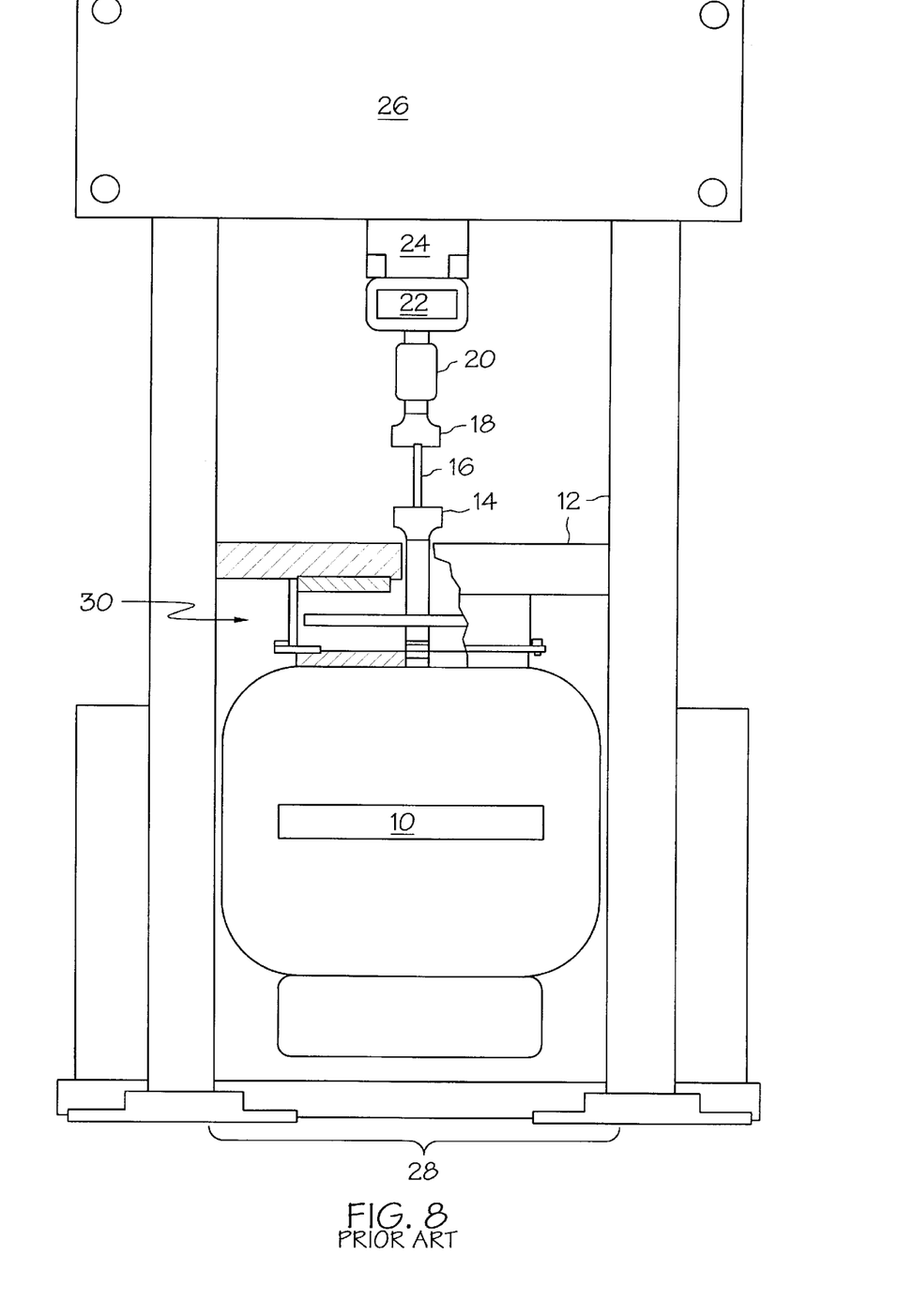
FIG. 8 is a schematic illustration of a conventional mechanical test system.

A conventional mechanical test system, commonly known as the Unholtz-Dickie test frame, is illustrated in FIG. 8. The conventional system utilizes an electrodynamic shaker 10 mounted to a support 12 to produce periodic actuation of a first workpiece grip 14 and transfer a periodic load to a workpiece or specimen 16 held at its opposite end by a second grip 18. The load characteristics are sensed by a force gauge 20 and a conventional load cell 22. A workpiece alignment assembly 24 is provided to ensure precise alignment of the first and second grips 14, 18 along a common vertical axis. A 4500 lb (2025 kg) aluminum crosshead 26 is hydraulically clamped to the support 12 and the support 12 is supported on air pad feet 28. A pneumatic cylinder 30 is provided for applying an offset load to the workpiece 16 via the first grip 14.

The electrodynamic shaker 10 of the conventional system contains relatively high mass moving parts, e.g. an armature assembly, which, typically, must be restrained by bearing arrangements. Transverse restraint of the armature and other moving parts must be provided to ensure uniform axial actuation. However, transverse restraints often limit the amount of input energy reaching the workpiece 16 because significant energy damping is introduced by the transverse restraints. Similarly, the mass of the moving parts of the conventional system limits the range of available loading frequencies, the response time of the actuation mechanism, and demands a significant amount of energy to produce mechanical actuation. Finally, because of the limitations of the conventional mechanical test system noted herein, a test workpiece may merely be periodically loaded at maximum accelerations ranging from 100 to 200 G (980–1960 m/s$^2$).

Accordingly, there is a need for an actuator wherein transverse restraint of the actuation element is not required, massive moving parts are eliminated, response time of the actuator is improved, a significant amount of input energy is transferred to the test workpiece, and wherein a test workpiece may be periodically loaded at maximum accelerations well above 100 to 200 G (980–1960 m/s$^2$).

BRIEF SUMMARY OF THE INVENTION

This need is met by the present invention wherein a magnetostrictive element and a high frequency magnetostrictive actuator utilizing the magnetostrictive element are provided. In operation, transverse restraint of the actuation element is not required, massive moving parts are eliminated, and response time of the actuator is improved.

In accordance with one embodiment of the present invention, a magnetostrictive actuator is provided comprising an actuator base, a magnetostrictive assembly, an actuator frame, and a flexible disk. The magnetostrictive assembly includes a magnetostrictive element having a first magnetostrictive element end portion, a second magnetostrictive element end portion, and a magnetostrictive element body defined between the first and second magnetostrictive element end portions. The first magnetostrictive element end portion is mechanically coupled to a first surface of the actuator base and the magnetostrictive element body extends from the actuator base in a first direction. The actuator frame includes a first frame portion and a second frame portion. The first frame portion is mechanically coupled to the actuator base. The flexible disk includes a perimetrical disk portion and a bearing surface portion. The perimetrical disk portion is mechanically coupled to the second frame portion and the bearing surface portion is mechanically coupled to the second magnetostrictive element end portion.

The perimetrical disk portion defines a flexible disk span and the bearing surface portion defines a bearing surface span. The bearing surface span may extend along at least about 10% of the flexible disk span and preferably extends along about 38% of the flexible disk span. The bearing surface span may be substantially centered within the flexible disk span.

The magnetostrictive assembly may further include a magnetic coil unit surrounding the magnetostrictive element and a coil cooling assembly thermally coupled to the magnetic coil unit. A magnetic flux path in communication with the magnetic coil may be formed in the actuator base and the actuator frame.

The actuator frame may comprise an actuator enclosure including a first enclosure end portion, a second enclosure end portion, and an enclosure body defined between the first and second enclosure end portions. The first enclosure end portion may be mechanically coupled to the first surface of the actuator base, the second enclosure end portion may define an enclosure rim portion, the enclosure body may extend from the actuator base in the first direction, the perimetrical disk portion may be mechanically coupled to the enclosure rim portion, and the bearing surface portion may be mechanically coupled to the second magnetostrictive element end portion. The enclosure body may comprise a cylindrical body.

The second frame portion may comprise a flexible disk clamping assembly operative to forcibly bias the bearing surface portion against the second magnetostrictive element end portion. The flexible disk clamping assembly may comprise a pair of clamping rings positioned on opposite sides of the flexible disk substantially aligned with the perimetrical disk portion.

In accordance with another embodiment of the present invention, a magnetostrictive actuator is provided comprising a magnetostrictive material portion and a plurality of cooling fluid bores formed within the magnetostrictive material portion. The cooling fluid bores may be oriented substantially parallel to the magnetostrictive material portion axis. A constrictive sheath may surround the magnetostrictive material portion. The constrictive sheath may comprise a tensioned strand wound about the magnetostrictive material. The magnetostrictive material portion may comprise a pair of magnetostrictive material sub-portions coupled to one another in an end-to-end relation along the magnetostrictive material portion axis.

In accordance with yet another embodiment of the present invention, a magnetostrictive actuator is provided comprising an epoxy matrix, a plurality of cooling fluid bores formed within the epoxy matrix, and a plurality of magnetostrictive rods formed within the epoxy matrix and extending generally parallel to the magnetostrictive element axis from the first magnetostrictive element end portion to the second magnetostrictive element end portion. The cooling fluid bores may extend generally parallel to the magnetostrictive element axis and may extend from the first magnetostrictive element end portion to the second magnetostrictive element end portion. A volume defined by the magnetostrictive element may comprise approximately six parts epoxy matrix, three parts magnetostrictive rods, and one part cooling fluid bores. The quantity of magnetostrictive rods may be approximately three times greater than the quantity of the plurality of cooling fluid bores. The cooling fluid bores may define respective substantially star shaped cross sections.

Accordingly, it is an object of the present invention to provide a magnetostrictive element and a high frequency magnetostrictive actuator utilizing the magnetostrictive element, wherein transverse restraint of the actuation element is not required, massive moving parts are eliminated, response time of the actuator is improved, a significant amount of input energy is transferred to the test workpiece, and wherein a test workpiece may be periodically loaded at maximum accelerations well above 100 to 200 G (980–1960 m/s$^2$).

DETAILED DESCRIPTION OF THE INVENTION

Figure 1:
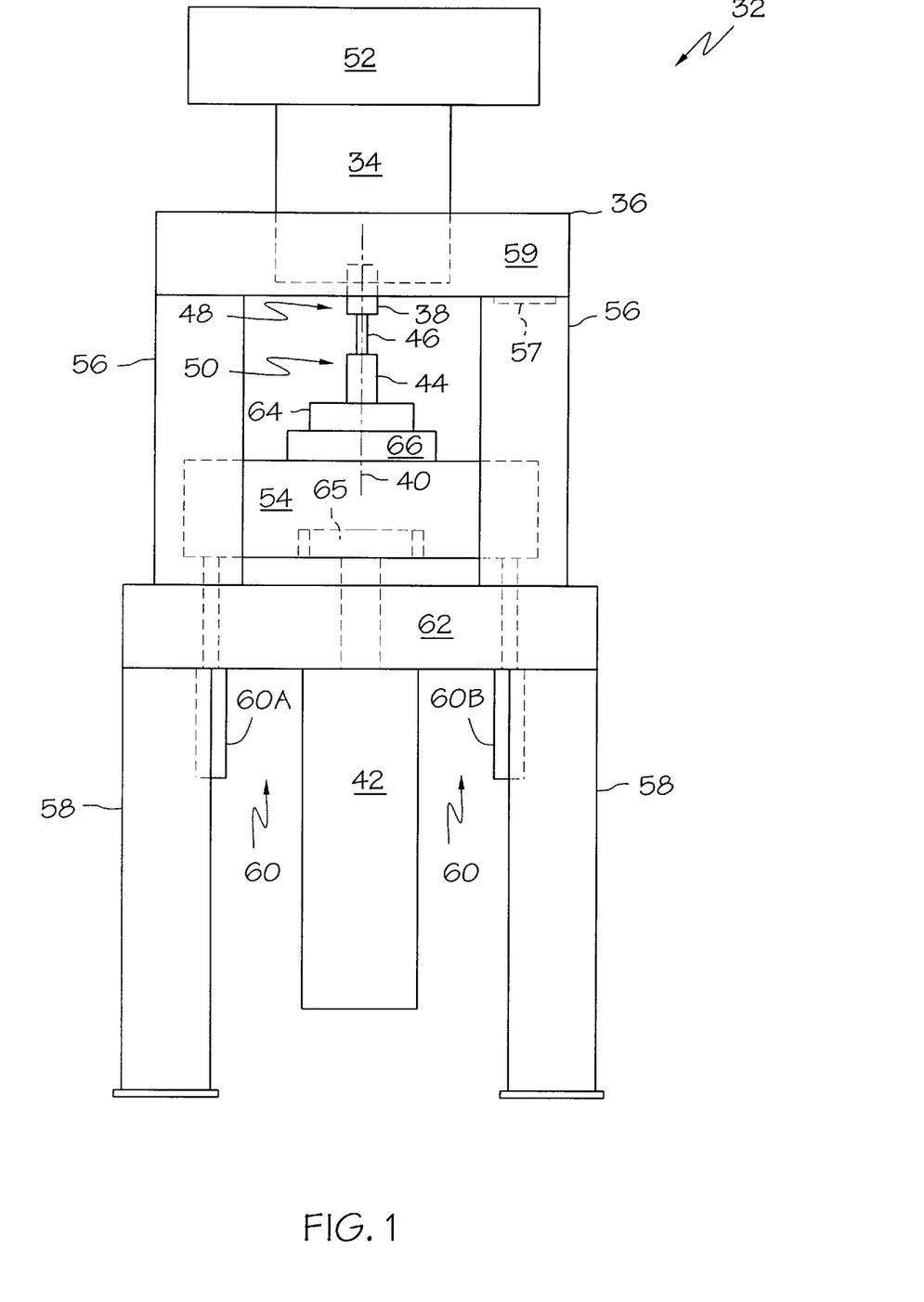
FIG. 1 is a schematic illustration of a mechanical test system according to the present invention.

Referring initially to FIG. 1, a mechanical test system 32 is illustrated. A primary actuator 34 is mechanically coupled to a test system frame 36 and is arranged to move a first specimen holder 38 back and forth along a linear, preferably vertical, axis of actuation 40. A secondary actuator 42 is mechanically coupled to the test system frame 36 and is arranged to displace a second specimen holder 44 along the axis of actuation 40. A test specimen 46 secured to the first and second specimen holders 38, 44 is placed under periodic tension or compression by activating the primary and secondary actuators 34, 42.

To avoid the disadvantages of the conventional test devices described herein, the primary actuator 34 comprises a solid state actuation element, preferably a magnetostrictive material. A solid state actuation element, as referenced in the present specification and claims, comprises any member capable of creating linear movement or displacement with the use of a single motion producing element. A detailed description of the specific structure of the primary actuator 34 is presented herein with reference to FIGS. 3, 4A, 4B, 5A, and 5B. The secondary actuator is preferably a servo-hydraulic actuator but may be any actuator capable of producing the load and loading frequencies described herein. A suitable servo-hydraulic actuator is available from MTS Systems Corporation, Minneapolis, Minn., and includes a servo valve (product no. 252.24C), a 3000 psi manifold (product no. 298.12C), and a 100 kN actuator.

The first specimen holder 38 is adapted to secure a first end 48 of the test specimen 46 and the second specimen holder 44 is adapted to secure a second end 50 of the test specimen 46. To ensure that the specimen holders 38, 44 are aligned along the axis of actuation 40, an alignment device 66 is mechanically coupled to the second specimen holder 44 and may, alternatively, be coupled to the first specimen holder 38. The primary actuator 34, which is arranged to mechanically move or displace the first specimen holder 38, comprises a high frequency actuator and the secondary actuator 42, which is arranged to mechanically move the second specimen holder 44, comprises a low frequency actuator. Specifically, the primary or high frequency actuator 34 is capable of producing a primary load at frequencies up to 2000 Hz and the secondary or low frequency actuator is capable of producing a secondary load at frequencies less than 20 Hz.

In the illustrated embodiment, the magnitude of the primary load is approximately 6 kN or less in tension or 6 kN or less in compression. The magnitude of the secondary load is approximately 25 kN or less in tension or 25 kN or less in compression. Superimposed high and low frequency loading of the test specimen 46 is achieved by simultaneously activating the primary and secondary actuators 34, 42. Additionally, a static offset load is created by controlling the secondary actuator 42 to produce a relatively constant load in tension or compression while controlling the primary actuator 34 to produce the aforementioned high frequency loading. The secondary actuator 42 may also be utilized to position the second specimen holder 44 relative to the first specimen holder 38 so as to adjust the test system 32 to accommodate test specimens 46 of varying lengths and to absorb any specimen elongation occurring during loading.

A load cell 64 is arranged to measure actuation forces exerted upon the test specimen 46. An auxiliary load cell 65, although not crucial to the operation of the system, is positioned in direct communication with the secondary actuator 42 to provide an alternative reference point for monitoring the loads induced in the system 32. The load cell 64 and the auxiliary load cell 65 may be any one of a number of commercially available load cells. In the illustrated embodiment, a pair of 100 kN load cells available from Eaton of Troy, Michigan, under product number 3174, are utilized.

To confine vibrations created by the primary and secondary actuators 34, 42 a first isolation mass 52 is mechanically coupled to the primary actuator 34 and a second isolation mass 54 is mechanically coupled to the second specimen holder 44. The first and second isolation masses 52, 54 are arranged such that the first and second specimen holders 38, 44 and the primary actuator 34 are positioned between the first and second isolation masses 52, 54 along the axis of actuation 40. Each isolation mass weighs approximately 900 lb (405 kg). Additionally, the mass of the test system frame 36 comprising 200 lb (90 kg) cast iron upper frame posts 56, 350 lb (160 kg) cast iron lower frame posts 58, a 1200 lb (540 kg) steel machine crosshead 59, and an 1800 lb (810 kg) steel machine platen 62, further isolates the vibrations. The overall height of the test system 32 is approximately 79" (200 cm).

To ensure that the vibrations created by the primary and secondary actuators 34, 42 do not cause resonant vibratory motion of any components in the vicinity of the actuators 34, 42, each component positioned between the first and second isolation masses 52, 54, i.e. each component subject to un-damped or non-isolated vibrations, is constructed to be non-resonant below the maximum vibrational frequency of the primary actuator 34. For example, where the maximum vibrational frequency of the primary actuator 34 is 2000 Hz, each mounting bolt used to secure the primary actuator 34 to the machine crosshead 59 is fashioned so as to avoid resonance below 2000 Hz. Similarly, each component utilized within the primary actuator is fashioned so as to be non-resonant below 2000 Hz. Additionally, support edges of the upper frame posts 56 and the lower frame posts 58 each include a 1/32" (0.8 mm) post cut-out 57 to further secure the weight of the various members of the test system 32 and prevent undesirable vibrations and instabilities throughout the test system 32.

As an operational safeguard, an auxiliary lift assembly 60 is mechanically coupled to the second isolation mass 54 and is adapted to support the second isolation mass 54 independent of the secondary actuator 42 particularly in the event of a power failure. The auxiliary lift assembly 60 may also be employed during specimen loading to reduce the load upon the secondary actuator 42. Specifically, a pair of pneumatic lifts 60a, 60b, are secured to the machine platen 62 and include pneumatic actuators extending through the machine platen 62 and secured to the second isolation mass 54. In the illustrated embodiment, a pair of 600 lb (270 kg) capacity pneumatic lifts are employed.

It is contemplated by the present invention that a variety of auxiliary monitoring and testing devices may be coupled to the test specimen 46 and/or the mechanical test system 32 without departing from the scope of the present invention. For example, strain gauges and crack sensors may be coupled to the test specimen and/or a specimen temperature control unit may be coupled to the test system 32.

Figure 2:
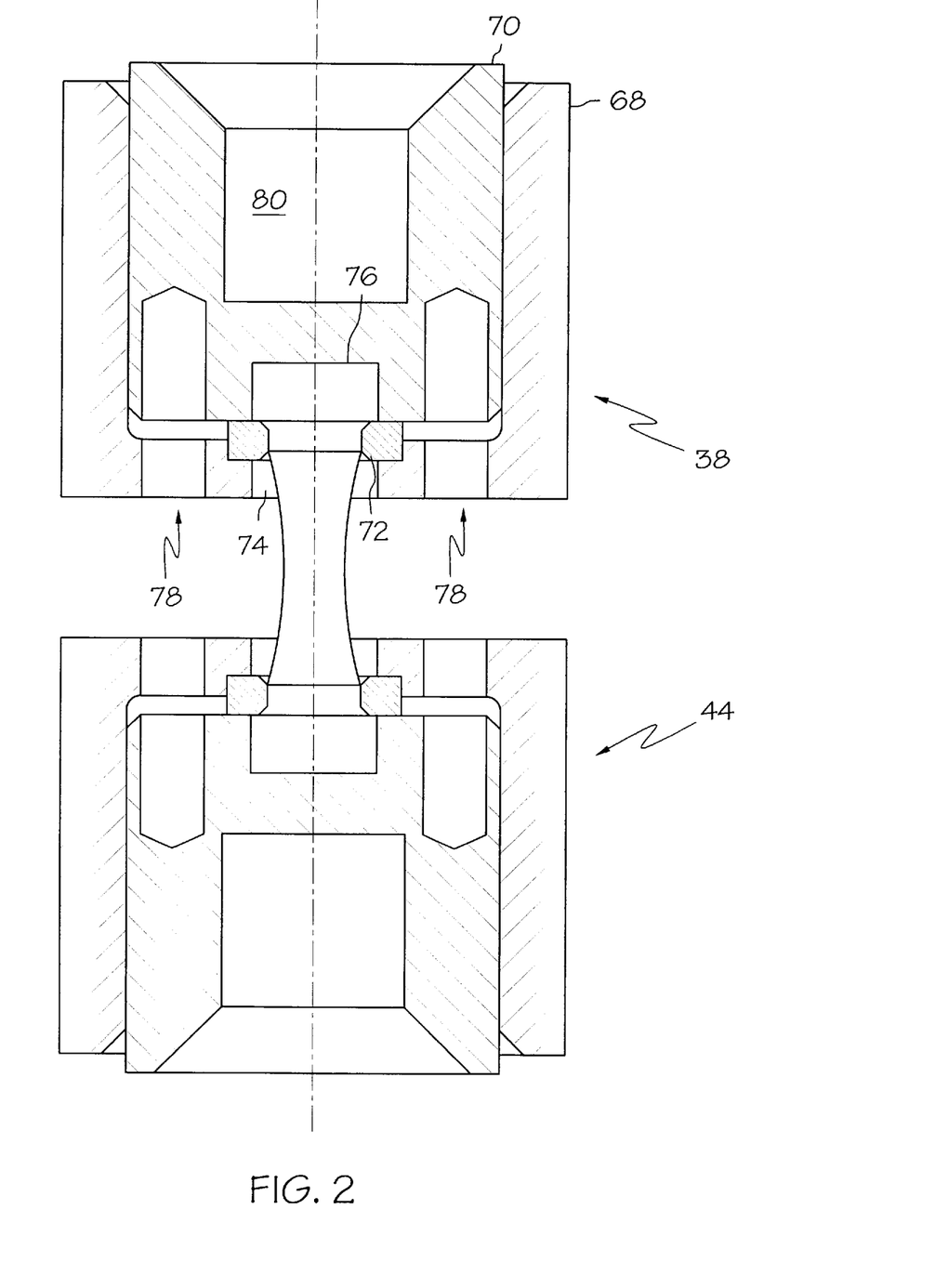
FIG. 2 is a cross-sectional view of a pair of specimen holders according to the present invention.

Referring now to FIG. 2, the first and second specimen holders 38, 44 are described. The structure of the first specimen holder 38 is identical to that of the second specimen holder 44. Accordingly, for the purposes of the present specification, reference is only made to the structure of the first specimen holder 38. Further, since FIG. 2 is a cross sectional view of the first and second specimen holders 38, 44 it should be noted that the orthogonal cross section of the first and second specimen holders 38, 44 is circular. Similarly, the test specimen 46, which is not shown in cross section, and a grip flange 72, also define corresponding circular cross sections.

The first specimen holder 38 includes an outer grip ring 68, an inner grip ring 70, and a grip flange 72. The outer grip ring 68 includes a specimen end passage 74 sized so as to enable passage of the first specimen end 48 there through. The inner grip ring 70 includes a specimen end receiving recess 76 sized to closely fit the outside diameter of the first specimen end 48. Specifically, the specimen end receiving recess 76 is approximately 0.001" (0.0254 mm) larger than the outer diameter of the first specimen end 48. The grip flange 72 comprises a split ring assembly which is placed about the test specimen 46 after the first specimen end 48 is passed through the specimen end passage 74 and before the outer grip ring 68 is placed about the inner grip ring 70. The grip flange, when placed about the test specimen 46, prevents the first specimen end 48 from passing back through the specimen end passage 74. The outer grip ring 68 is secured to the inner grip ring 70 with threaded bolts engaged in four securing bores 78, only two of which are shown, or in any other conventional manner. Finally, to enable attachment of the first specimen holder 38 to the primary actuator 34, a threaded attachment bore 80 is provided in the inner grip ring 70.

Figure 3:
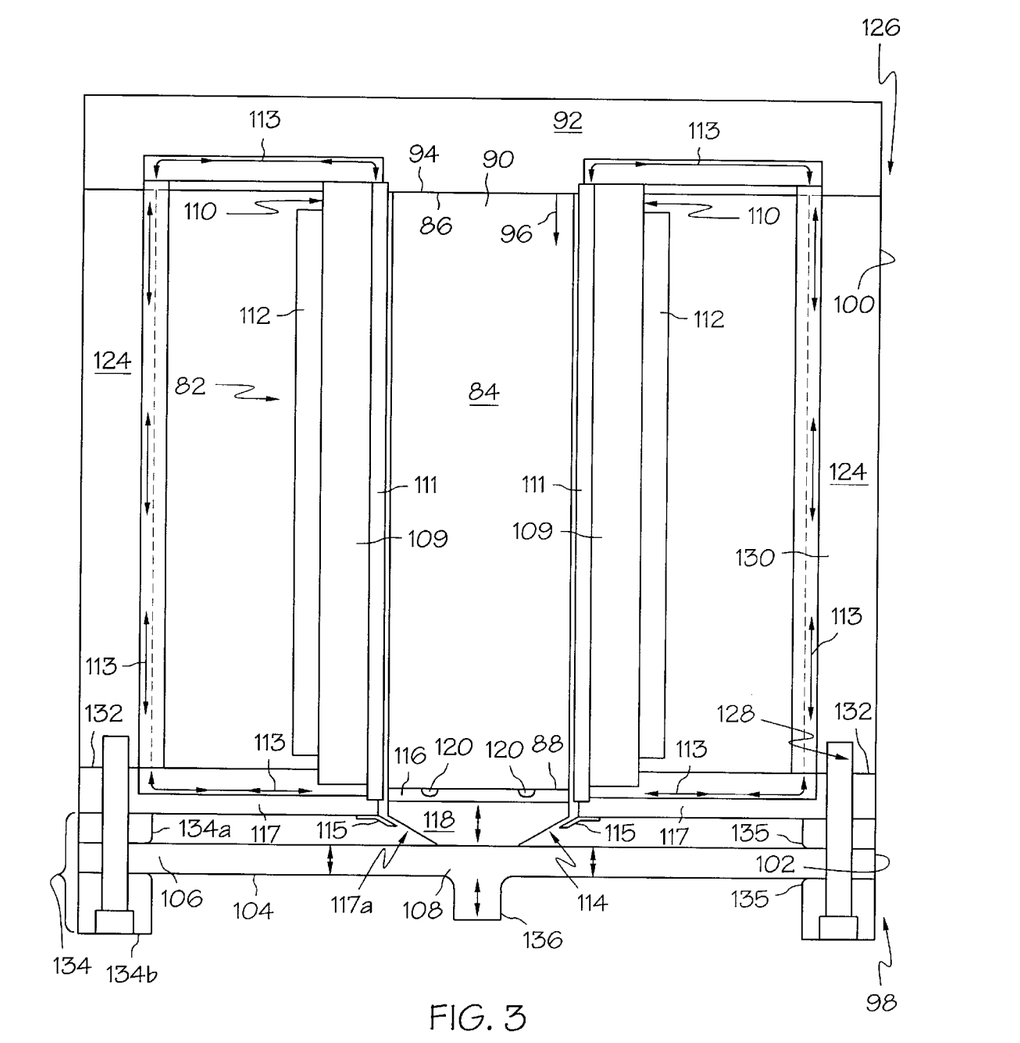
FIG. 3 is a schematic illustration of a magnetostrictive actuator according to the present invention.

Referring now to FIG. 3 a specific embodiment of the primary actuator 34 is described. Since FIG. 3 is a plan view of the primary actuator 34 it should be noted that the cross section of the primary actuator 34, and the majority of its components, is symmetrical and circular. A magnetostrictive assembly 82 includes a magnetostrictive element 84 having a first magnetostrictive element end portion 86, a second magnetostrictive element end portion 88, and a magnetostrictive element body 90 defined between the first and second magnetostrictive element end portions 86, 88. The first magnetostrictive element end portion 86 is mechanically coupled to a first surface 94 of a steel actuator base 92. The magnetostrictive element body 90 extends from the actuator base 92 in a first direction 96 substantially perpendicular to the actuator base 92.

A steel actuator frame 98 includes a first frame portion 100 and a second frame portion 102. The first frame portion 100 is mechanically coupled to the actuator base 92. A flexible disk 104 includes a perimetrical disk portion 106 mechanically coupled to the second frame portion 102 and a bearing surface portion 108 mechanically coupled to the second magnetostrictive element end portion 88. The bearing surface portion 108 is bounded by that region of the flexible disk 104 which is directly mechanically coupled to the magnetostrictive element 84. In the illustrated embodiment, the bearing surface portion 108 is directly mechanically coupled to the magnetostrictive element 84 via a flexible disk engaging plate 118. In the illustrated embodiment, the flexible disk 104 is an aluminum disk about 13 mm thick and having a diameter of approximately 250 mm, but may be formed of any material and may have any dimensions and shape resulting in a flexible structure and an axially actuable bearing surface portion.

A magnetic coil unit 110 surrounds the magnetostrictive element 84 and is secured between the actuator base 92 and a steel coil unit support plate 117. As will be appreciated by those skilled in the art the magnetic coil unit comprises potted windings 109 wound around a cylindrical core 111 of, e.g, PVC. A coil cooling assembly 112 is thermally coupled to the magnetic coil unit 110. A magnetic flux path, indicated generally by the arrows 113, is provided in communication with the magnetic coil unit 110 and is positioned in cut-outs formed in the actuator base 92, the actuator frame 98, and the coil unit support plate 117. Typically, the flux path 113 comprises laminated standard transformer silicon steel portions arranged to provide enough capacity for the magnetic flux generated by the coil unit 110. In the embodiment illustrated in FIG. 3, the flux path is defined by 0.75" by 0.007" (19.1 mm by 0.18 mm) laminate layers arranged to form a path having a width of about 3" (76.2 mm). The coil cooling assembly 112 may comprise any conventional thermally conductive cooling arrangement. For example, coolant carrying copper tubes embedded in a thermally conductive epoxy, e.g. an aluminum filled epoxy, can be thermally coupled to the magnetic coil unit 110. Fluid may be carried to the copper tubes through coolant ports provided in the actuator frame 98.

The magnetostrictive assembly further includes an aluminum end cap assembly 114 mechanically coupled to the second magnetostrictive element end portion 88. The end cap assembly 114 comprises a sealing plate 116 and the flexible disk engaging plate 118 which extend through a central support plate aperture 117*a* formed in the coil unit support plate 117. The sealing plate 116 includes at least one cooling fluid passage 120 in communication with longitudinal cooling fluid bores 146 formed in the magnetostrictive element 84, see FIGS. 4A and 4B.

A trap ring 115 is secured, preferably bolted, to the coil unit support plate 117 about the support plate aperture 117*a*. The trap ring 115 is generally shaped as a truncated cone and extends inside of the circumference of the flexible disk engaging plate 118. If the flexible disk 104 fails, i.e., cracks and/or breaks away from the actuator frame 98, the trap ring 115 will support the magnetostrictive element 84 within the actuator frame 98 and prevent damage to the magnetostrictive element 84.

The actuator frame 98 comprises an actuator enclosure 124 including a first enclosure end portion 126, a second enclosure end portion 128, and a cylindrical enclosure body 130 defined between the first and second enclosure end portions 126, 128. The first enclosure end portion 126 is mechanically coupled to the first surface 94 of the actuator base 92. The second enclosure end portion 128 defines an enclosure rim portion 132. The enclosure body 130 extends from the actuator base in the first direction 96. The perimetrical disk portion 106 is mechanically coupled to the enclosure rim portion 132 and the bearing surface portion 108 is mechanically coupled to the second magnetostrictive element end portion 88.

The second frame portion 102 comprises a flexible disk clamping assembly 134 operative to forcibly bias the bearing surface portion 108 against the second magnetostrictive element end portion 88 and longitudinally compress the magnetostrictive element 84. Specifically, where the magnetostrictive element 84 is approximately 10" (25.4 cm) in length, the flexible disk clamping assembly 134 is operative to produce a force on the order of about 50 kN and compress the magnetostrictive element 84 on the order of about 1 mm. As will be appreciated by those of ordinary skill in the art, this longitudinal compression is necessary for proper actuation of the magnetostrictive element 84 and the optimal magnitude of the compressive force may vary among different applications and designs.

The flexible disk clamping assembly 134 comprises a pair of clamping rings 134*a*, 134*b* positioned on opposite sides of the flexible disk 104 and substantially aligned with the perimetrical disk portion 106. The pair of clamping rings 134*a*, 134*b* include rounded inner edge portions 135 so as to permit flexion of the flexible disk 104. The flexible disk 104 further includes an attachment stud 136 provided in the bearing surface portion 108.

A first application of the actuator of the present invention is as a stand alone shaker, where an item to be shaken is secured to the attachment stud 136 and the actuator base 92 is secured to a relatively large mass. In this embodiment the actuator could be used to accelerate the item in pulsed, sinusoidal, or random fashion. A second application of the actuator is as a micro-positioner. The flexible disk 104 allows extremely repeatable linear motion without the risk of transverse motion or frictional stick-slip behavior that would result from the use of bearings or bushings.

In operation, an oscillating magnetic field, e.g., approximately 2000 Hz, is created by driving the coil at a selected frequency and amplitude, e.g., approximately 10 Amps.

Higher driving currents may be supplied if adequate coil and magnetostrictive element cooling is provided. The magnetic field produces high frequency positive and negative actuation of the magnetostrictive element 84 and causes the flexible disk 104 and its attachment stud 136 to advance and retract on the order of about 0.1 mm in either the positive or the negative direction. Accordingly, the primary actuator may be employed to produce high frequency back and forth movement, tension, or compression of any of a wide variety of specimens coupled to the attachment stud 136. The coil 110 may be driven by any of a variety of conventional power amplifier circuits arranged to produce the driving current described herein. It is contemplated by the present invention that, depending upon the specific application of the actuator of the present invention, the coil may be driven at a variety of frequencies higher and lower than 2000 Hz or at a steady state.

Figure 7A:
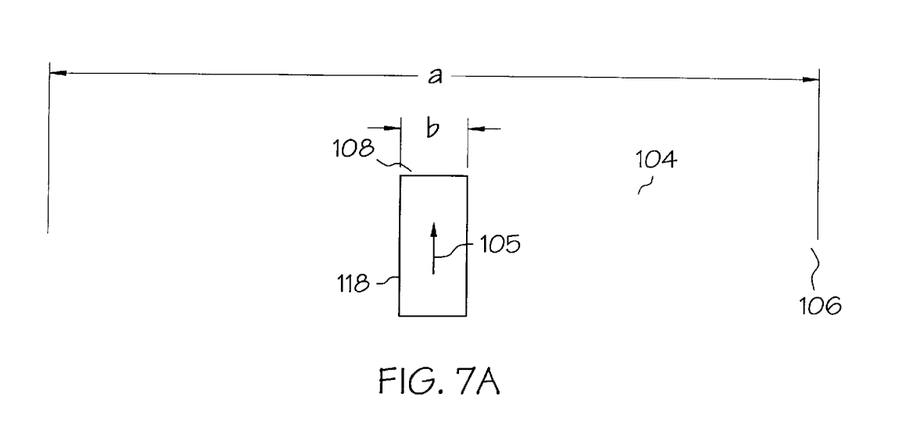
FIGS. 7A and 7B are schematic illustrations of a magnetostrictive actuator according to two alternative embodiments of the present invention.
Figure 7B:
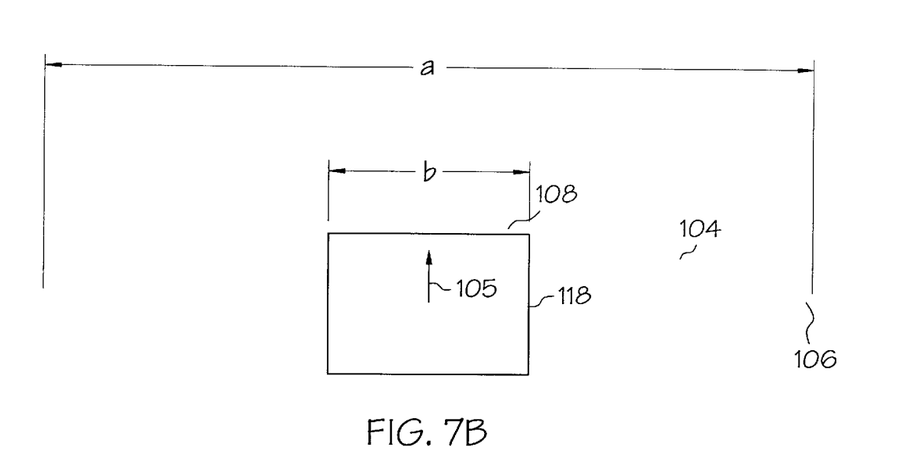

The flexible disk 104, the perimetrical disk portion 106, the bearing surface portion 108, and the flexible disk engaging plate 118 are illustrated schematically in FIGS. 7A and 7B. The perimetrical disk portion 106 defines a flexible disk span a and the bearing surface portion 108 defines a bearing surface span b. In the embodiment illustrated in FIG. 7A the bearing surface span b extends along at least about 10% of the flexible disk span a. A cantilever effect results from actuation of the flexible disk engaging plate 118 in the positive direction 105 since the bearing surface span b extends along a predetermined length of the flexible disk span a and is not merely a point source of mechanical actuation. Specifically, as a result of the cantilever effect, upon actuation of the flexible disk engaging plate 118 in the positive direction 105, a central portion 107 of the flexible disk 104 moves a greater linear distance than the flexible disk engaging plate 118. The cantilever effect is exaggerated where the bearing surface span b extends along about 38% of the flexible disk span a, as is illustrated in FIG. 7B.

Figure 4A:
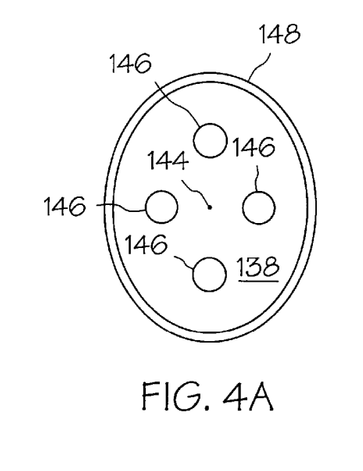
FIGS. 4A and 4B are top and side plan views, respectively, of a magnetostrictive element according to the present invention.
Figure 4B:
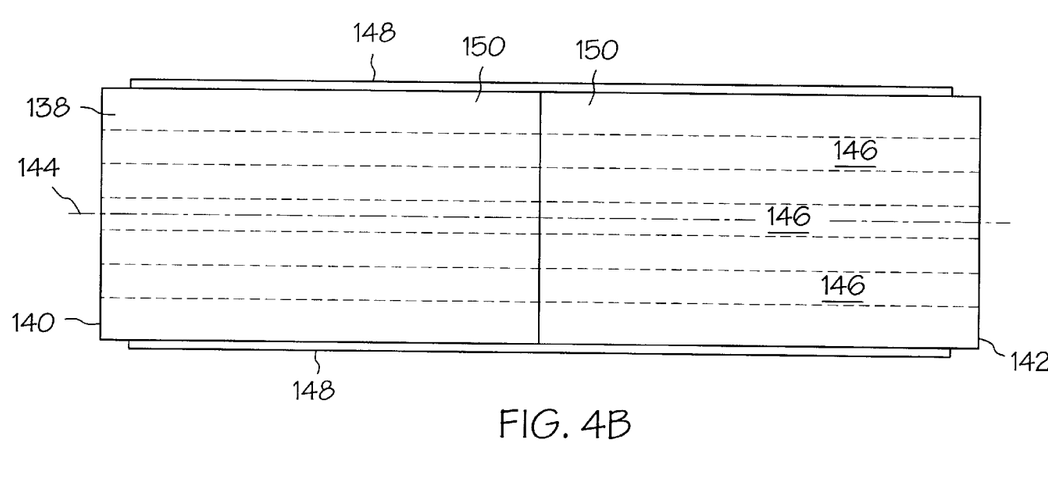

Referring now to FIGS. 4A, 4B, 5A, 5B, and 6, three alternative magnetostrictive element arrangements are illustrated. In FIGS. 4A and 4B, a magnetostrictive material portion 138 defines a first magnetostrictive element end portion 140, a second magnetostrictive element end portion 142, and a magnetostrictive material portion axis 144 extending between the first and second magnetostrictive element end portions 140, 142. A plurality of cooling fluid bores 146 are formed within the magnetostrictive material portion 138 and are oriented substantially parallel to the magnetostrictive material portion axis 144.

It is contemplated by the present invention that the performance of the magnetostrictive element 84 corresponds roughly to its size. However, the size of commercially available magnetostrictive elements is limited. Accordingly, to increase the effective length of the magnetostrictive material portion 138, a pair of magnetostrictive material sub-portions 150 are bonded or otherwise coupled to one another in an end-to-end relation along the magnetostrictive material portion axis 144. The approximate dimensions of the magnetostrictive material portion 138 are as follows: 10" (25.4 cm) in length; 2.85" (7.25 cm) cross section major axis; and 2.2" (5.6 cm) cross section minor axis. The cooling fluid bores 146 are spaced 1.5" (3.75 cm) apart along the major axis of the cross section and 1.25" (3.25 cm) apart along the minor axis of the cross section.

To minimize the deleterious effects of magnetic field eddy currents within the magnetostrictive material portion 138, the magnetostrictive material portion 138 comprises a laminate including a plurality of bonded magnetostrictive layers oriented substantially parallel to the magnetostrictive material portion axis 144. Preferably, the maximum lamination thickness is approximately 0.20" (0.5 cm). The elliptical shape of the cross section results from cutting a pre-manufactured magnetostrictive rod of circular cross section and bonding the layers, as cut, to form a unitary body having an elliptical cross section. A widely available magnetostrictive material known as TERFENOL-D™ and a suitable epoxy for bonding individual layers of TERFENOL-D™ are available from Etrema Products, Ames, Iowa.

To maintain the integrity of the magnetostrictive material portion 138 over extended use and to improve the axial nature of its actuation, a constrictive sheath 148, forcibly biased towards the magnetostrictive material portion axis 144, surrounds the magnetostrictive material portion 138. The constrictive sheath 148 preferably comprises a tensioned strand wound about the magnetostrictive material portion 138.

For example, KEVLAR™ thread tensioned at 15–20 lbs (6.75–9.0 kg) and secured in an epoxy matrix, e.g., an aluminum filled epoxy or any other suitable epoxy, is wound about the magnetostrictive material portion 138 to form four layers of the thread along substantially the entire length of the magnetostrictive material portion 138.

Figure 5A:
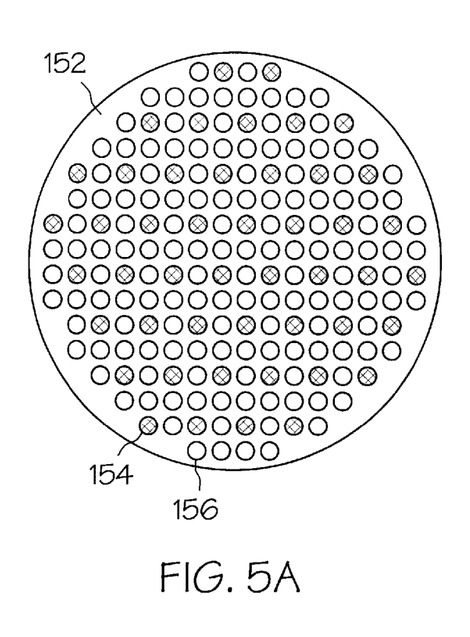
FIGS. 5A and 5B are top and side plan views, respectively, of a magnetostrictive element according an alternative embodiment of the present invention.
Figure 5B:
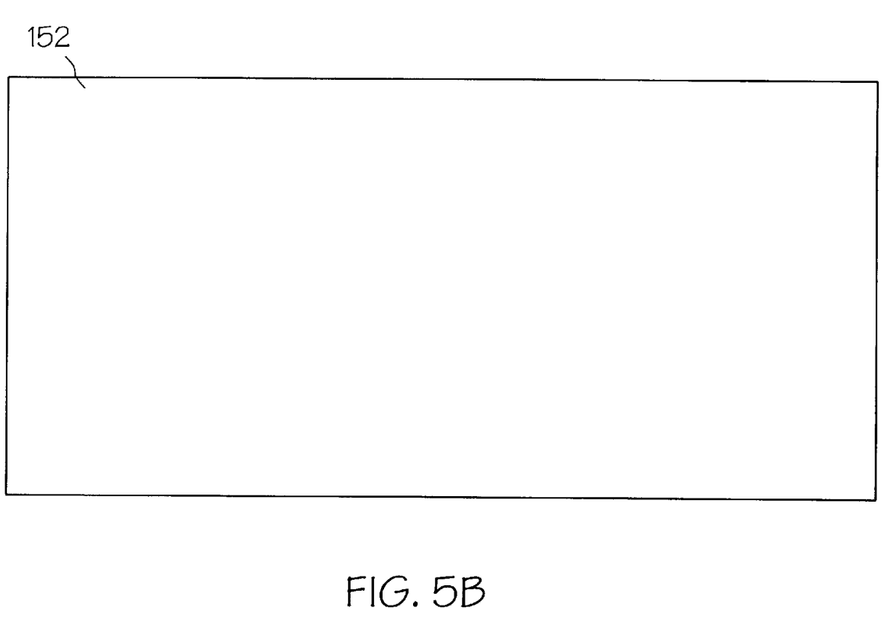

In the magnetostrictive element illustrated in FIGS. 5A and 5B, where like elements are indicated by like reference numerals and where hidden structure is not illustrated in phantom, an epoxy matrix 152 extends along the magnetostrictive element axis 144 from a first magnetostrictive element end portion 140 to a second magnetostrictive element end portion 142. A plurality of cooling fluid bores 154 are formed within the epoxy matrix 152 and extend generally parallel to the magnetostrictive element axis 144 from the first magnetostrictive element end portion 140 to the second magnetostrictive element end portion 142. A plurality of magnetostrictive rods 156 are embedded within the epoxy matrix 152 and also extend generally parallel to the magnetostrictive element axis 144 from the first magnetostrictive element end portion 140 to the second magnetostrictive element end portion 142.

The volume defined by the magnetostrictive element 84 comprises approximately six parts epoxy matrix 152, three parts magnetostrictive rods 156, and one part cooling fluid bores 154. The quantity of the magnetostrictive rods 156 is approximately three times greater than the quantity of the cooling fluid bores 154. Preferably, the magnetostrictive rods 156 are arranged in a uniform distribution across the cross section of the magnetostrictive element. Similarly, to ensure adequate cooling of the magnetostrictive rods 156, the cooling fluid bores 154 are uniformly distributed in relation to the plurality of magnetostrictive rods 156. The rods 156 and bores 154 have cross sectional diameters on the order of approximately 0.20" (0.51 cm) and are spaced apart, center-to-center, by approximately 0.275" (0.70 cm). The approximate dimensions of the magnetostrictive element are as follows: 10" (25.4 cm) in length; and 4.5" (11.5 cm) circular cross section diameter.

Figure 6:
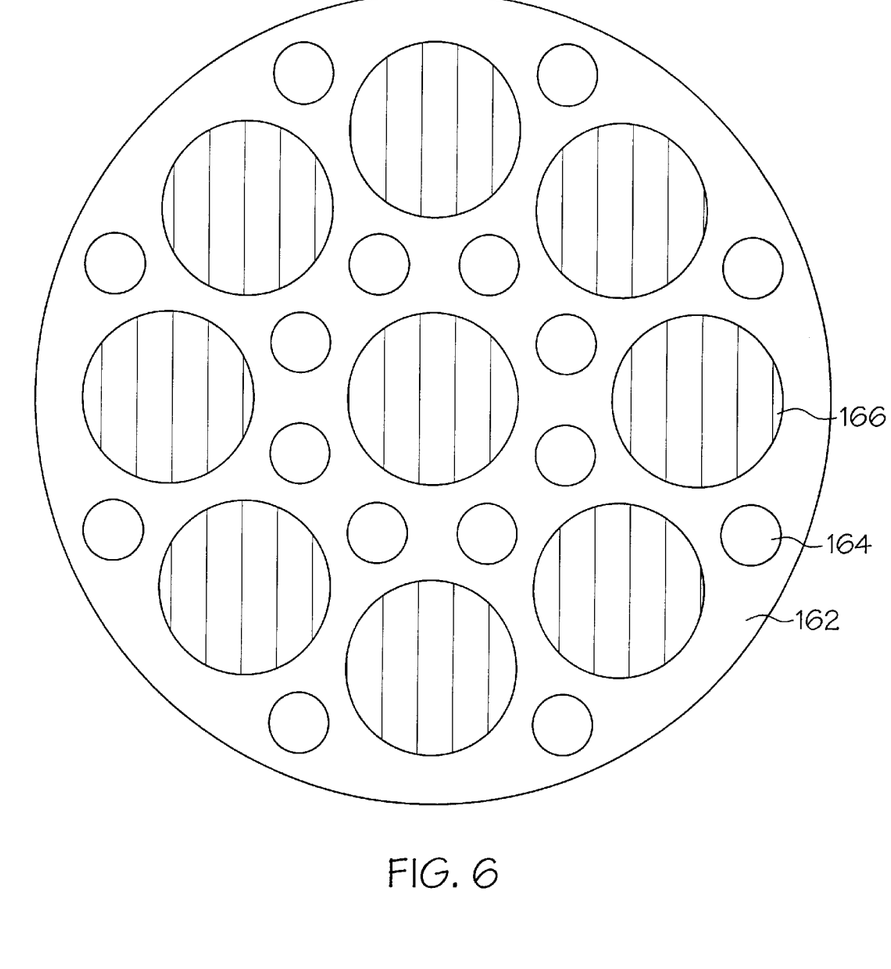
FIG. 6 is a top view of a magnetostrictive element according to a further alternative embodiment of the present invention.

In the magnetostrictive element illustrated in FIG. 6, an epoxy matrix 162 extends along the magnetostrictive element axis. A plurality of cooling fluid bores 164 are formed within the epoxy matrix 162 and extend generally parallel to the magnetostrictive element axis. A plurality of magnetostrictive laminate rods 166 are embedded within the epoxy matrix 162 and also extend generally parallel to the magnetostrictive element axis.

The magnetostrictive elements of FIGS. 5A, 5B, and 6 may be constructed by securely positioning the magnetostrictive rods 156, 166 in a mold. Wax rods are also securely arranged in the mold in positions corresponding to the intended positions of the cooling fluid bores 154, 164. Material forming the epoxy matrix 152, 162 is then poured into the mold to form the solid state structure of the magnetostrictive element. The solid state structure is preferably wrapped with KEVLAR™ thread and more epoxy. The wax is melted out of the structure to form the cooling fluid bores 154, 164 and the ends of the structure are machined flat and parallel to each other.

According to one preferred aspect of the present invention, the cooling fluid bores 154, 164 may have a star shaped cross section with rounded corners to increase the surface area of the cooling fluid bores 154, 164.

It is contemplated by the present invention that although certain components described herein are identified as comprising aluminum, steel, or cast iron, a variety of materials may be used to form the components without departing from the scope of the present invention.

Having described the invention in detail and by reference to preferred embodiments thereof, it will be apparent that modifications and variations are possible without departing from the scope of the invention defined in the appended claims.

What is claimed is:

1. A magnetostrictive actuator comprising:

an actuator base;

a magnetostrictive assembly including a magnetostrictive element having a first magnetostrictive element end portion, a second magnetostrictive element end portion, and a magnetostrictive element body defined between said first and second magnetostrictive element end portions, wherein said first magnetostrictive element end portion is mechanically coupled to a first surface of said actuator base, and wherein said magnetostrictive element body extends from said actuator base in a first direction;

an actuator frame including a first frame portion and a second frame portion, wherein said first frame portion is mechanically coupled to said actuator base; and a flexible disk including a perimetrical disk portion and a bearing surface portion, wherein said perimetrical disk portion is mechanically coupled to said second frame portions, wherein said bearing surface portion is mechanically coupled to said second magnetostrictive element end portion, wherein said perimetrical disk portion defines a flexible disk span, wherein said bearing surface portion defines a bearing surface span, and wherein said bearing surface span extends along at least about 10% of said flexible disk span.

2. A magnetostrictive actuator comprising:

an actuator base;

a magnetostrictive assembly including a magnetostrictive element having a first magnetostrictive element end portion, a second magnetostrictive element end portion, and a magnetostrictive element body defined between said first and second magnetostrictive element end portions, wherein said first magnetostrictive element end portion is mechanically coupled to a first surface of said actuator base, and wherein said magnetostrictive element body extends from said actuator base in a first direction;

an actuator frame including a first frame portion and a second frame portion, wherein said first frame portion is mechanically coupled to said actuator base; and a flexible disk including a perimetrical disk portion and a bearing surface portion, wherein said perimetrical disk portion is mechanically coupled to said second frame portion and wherein said bearing surface portion is mechanically coupled to said second magnetostrictive element end portion, wherein said second frame portion comprises a flexible disk clamping assembly operative to forcibly bias said bearing surface portion against said second magnetostrictive element end portion.

3. A magnetostrictive actuator as set forth in claim 1 wherein said bearing surface span extends along about 38% of said flexible disk span.

4. A magnetostrictive actuator as set forth in claim 1 wherein said bearing surface span is substantially centered within said flexible disk span.

5. A magnetostrictive actuator as set forth in claim 1 wherein said magnetostrictive assembly further includes a magnetic coil unit surrounding said magnetostrictive element and a coil cooling assembly thermally coupled to said magnetic coil unit.

6. A magnetostrictive actuator as set forth in claim 5 wherein a magnetic flux path in communication with said magnetic coil is formed in said actuator base and said actuator frame.

7. A magnetostrictive actuator comprising:
an actuator base:
a magnetostrictive assembly including a magnetostrictive element having a first magnetostrictive element end portion, a second magnetostrictive element end portion, and a magnetostrictive element body defined between said first and second magnetostrictive element end portions, wherein said first magnetostrictive element end portion is mechanically coupled to a first surface of said actuator base, and wherein said magnetostrictive element body extends from said actuator base in a first direction:

an actuator frame including a first frame portion and a second frame portion, wherein said first frame portion is mechanically coupled to said actuator base; and a flexible disk including a perimetrical disk portion and a bearing surface portion, wherein said perimetrical disk portion is mechanically coupled to said second frame portion and wherein said bearing surface portion is mechanically coupled to said second magnetostrictive element end portion, wherein said actuator frame comprises an actuator enclosure including a first enclosure end portion, a second enclosure end portion, and an enclosure body defined between said first and second enclosure end portions, said first enclosure end portion is mechanically coupled to said first surface of said actuator base, said second enclosure end portion defines an enclosure rim portion, said enclosure body extends from said actuator base in said first direction, and wherein said perimetrical disk portion is mechanically coupled to said enclosure rim portion and said bearing surface portion is mechanically coupled to said second magnetostrictive element end portion.

8. A magnetostrictive actuator as set forth in claim 7 wherein said enclosure body comprises a cylindrical body.

9. A magnetostrictive actuator as set forth in claim 2 wherein said flexible disk clamping assembly comprises a pair of clamping rings positioned on opposite sides of said flexible disk substantially aligned with said perimetrical disk portion.

* * * * *

UNITED STATES PATENT AND TRADEMARK OFFICE
CERTIFICATE OF CORRECTION

PATENT NO : 5,877,432

DATED : March 2, 1999

INVENTOR(S) : George Anthony Hartman and James Raymond

It is certified that error appears in the above-identified patent and that said Letters Patent is hereby corrected as shown below:

Col. 11, line 25 "base:" should be --base;--.
Col. 11, line 35 "direction:" should be --direction;--.

Signed and Sealed this

Thirteenth Day of July, 1999

Attest:

Q. TODD DICKINSON

Attesting Officer

Acting Commissioner of Patents and Trademarks